(12) United States Patent
Otsuki

(10) Patent No.: US 10,544,723 B2
(45) Date of Patent: Jan. 28, 2020

(54) EXHAUST GAS ANALYSIS APPARATUS AND EXHAUST GAS ANALYSIS METHOD

(71) Applicant: HORIBA, Ltd., Kyoto (JP)

(72) Inventor: Yoshinori Otsuki, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 15/987,669

(22) Filed: May 23, 2018

(65) Prior Publication Data

US 2018/0340461 A1 Nov. 29, 2018

(30) Foreign Application Priority Data

May 24, 2017 (JP) .................................. 2017-102703

(51) Int. Cl.
| | |
|---|---|
| *F02B 27/04* | (2006.01) |
| *F01N 13/00* | (2010.01) |
| *G01N 1/22* | (2006.01) |
| *G01N 1/44* | (2006.01) |
| *F01N 3/08* | (2006.01) |

(52) U.S. Cl.
CPC ............. *F01N 13/008* (2013.01); *F01N 3/08* (2013.01); *G01N 1/2252* (2013.01); *G01N 1/44* (2013.01); *F01N 2560/05* (2013.01); *F01N 2560/07* (2013.01); *G01N 2001/2255* (2013.01)

(58) Field of Classification Search
CPC ........... F01N 3/08; F01N 13/008; G01N 1/44; G01N 1/2252

USPC .......................................................... 60/273
See application file for complete search history.

(56) References Cited

U.S. PATENT DOCUMENTS

| | | | |
|---|---|---|---|
| 3,593,023 A | 7/1971 | Dodson et al. | |
| 4,148,211 A | 4/1979 | Sawa et al. | |
| 6,460,400 B1* | 10/2002 | Ichikawa | ................ G01F 1/363 |
| | | | 73/114.71 |
| 2007/0151449 A1 | 7/2007 | Wohltjen et al. | |
| 2014/0338540 A1* | 11/2014 | Yoshimura | ........... G01N 1/2252 |
| | | | 96/413 |

FOREIGN PATENT DOCUMENTS

JP 2000259254 A 9/2000

OTHER PUBLICATIONS

EESR dated Oct. 5, 2018 issued for European Patent Application No. 18173850.1, 9 pgs.

* cited by examiner

*Primary Examiner* — Jason D Shanske
(74) *Attorney, Agent, or Firm* — Brooks Kushman P.C.

(57) ABSTRACT

An exhaust gas analysis apparatus includes an exhaust gas flow channel, a pump, and a heat exchanger. The exhaust gas flow channel is designed to permit passage of exhaust gas of an internal combustion engine, and is provided with an analysis device. The pump is disposed downstream of the analysis device in the exhaust gas flow channel. The heat exchanger is designed to receive at least one of heat of the pump and heat of exhaust gas passing downstream of the pump, and to use the heat to heat exhaust gas passing upstream of the pump in the exhaust gas flow channel.

16 Claims, 4 Drawing Sheets

EXHAUST GAS ANALYSIS APPARATUS AND EXHAUST GAS ANALYSIS METHOD

CROSS-REFERENCE TO RELATED APPLICATION

This application claims priority on Japanese Patent Application No. 2017-102703 filed on May 24, 2017, the disclosure of which is incorporated by reference herein.

BACKGROUND OF THE INVENTION

Field

The present disclosure relates to an exhaust gas analysis apparatus and an exhaust gas analysis method.

Background Art

As a conventional exhaust gas analysis apparatus, there is one which is configured to sample exhaust gas discharged from an internal combustion engine into an exhaust gas flow channel and introduce the exhaust gas into an analysis device, such as a filter, disposed in the exhaust gas flow channel, as disclosed in Patent Document 1.

When the exhaust gas is cooled in the exhaust gas flow channel and moisture (water vapor) in the exhaust gas condenses in the above exhaust gas analysis apparatus, there occurs, for example, a change in exhaust gas composition concentration due to a decrease in water vapor contained in the exhaust gas, and dissolution loss of a moisture soluble composition due to water droplets generation in the exhaust gas flow channel. Therefore, an upstream of the analysis device in the exhaust gas flow channel is being heated to a temperature at which no condensation of water vapor occurs.

However, a downstream of the analysis device in the exhaust gas flow channel has heretofore not been heated. For example, the exhaust gas is cooled during passage from the analysis device to a flowmeter. For this reason, moisture condenses in the downstream of the analysis device, and an error may occur in exhaust gas flow rate. This makes it difficult to highly accurately control, for example, a ratio (dividing ratio) of a flow rate of entire exhaust gas discharged from the internal combustion engine and a flow rate of exhaust gas introduced into the analysis device, resulting in low accuracy of analysis.

As a method of preventing moisture condensation in the downstream of the analysis device, it is conceivable to heat the downstream of the analysis device by a heater or the like. This, however, involves various problems, such as enlarged size and high cost of the apparatus, as well as increased power consumption and safety measures.

RELATED ART DOCUMENT

Patent Document

Patent Document 1: Japanese Unexamined Patent Publication No. 2000-259254

SUMMARY

It is an object of the present disclosure to prevent moisture condensation without causing the various problems, such as the enlarged size and high cost of the apparatus, and the increased power consumption.

Means of Solving the Problems

According to one aspect of the present invention, an exhaust gas analysis apparatus includes an exhaust gas flow channel, a pump, and a heat exchanger. The exhaust gas flow channel permits passage of exhaust gas of an internal combustion engine, and an analysis device is disposed therein. The pump is disposed downstream of the analysis device in the exhaust gas flow channel. The heat exchanger is designed to receive at least one of heat generated from the pump and heat of exhaust gas passing downstream of the pump, and to use the heat to heat exhaust gas passing upstream of the pump in the exhaust gas flow channel.

With the exhaust gas analysis apparatus so configured, the heat exchanger heats the exhaust gas passing upstream of the pump by using the heat of the pump and the heat of exhaust gas passing downstream of the pump. It is therefore possible to raise a temperature of the exhaust gas passing downstream of the analysis device without disposing a heater or the like. This makes it possible to prevent moisture condensation without causing, for example, the enlarged size and high cost of the apparatus, thereby reducing an error in exhaust gas flow rate due to the moisture condensation. For example, this leads to highly accurate control of a ratio (dividing ratio) of a flow rate of entire exhaust gas discharged from an internal combustion engine and a flow rate of exhaust gas introduced into the analysis device, thereby improving accuracy of analysis.

Furthermore, even though the heat generated from the pump has heretofore been wasted, the above configuration makes it possible to use effectively waste heat of the pump, thus leading to the high-efficient energy-saving apparatus.

In a specific embodiment, the heat exchanger includes a downstream-side heat transfer part and an upstream-side heat transfer part. The downstream-side heat transfer part is located downstream of the pump in the exhaust gas flow channel. The upstream-side heat transfer part is located upstream of the pump in the exhaust gas flow channel and placed in contact with the downstream-side heat transfer part.

With this configuration, it is possible to heat the exhaust gas passing upstream of the pump by using the configuration that the exhaust gas sucked by the pump is discharged after being heated by the heat of the pump itself.

At least one of the downstream-side heat transfer part and the upstream-side heat transfer part preferably includes a buffer space configured to reduce pressure fluctuations that may occur in the exhaust gas flow channel.

With this configuration, it is possible to impart a buffer function and a heat exchange function to the downstream-side heat transfer part and the upstream-side heat transfer part. That is, with this above configuration, it is possible to heat the exhaust gas passing upstream of the pump while reducing pressure fluctuations and noise caused by the pulsation of the pump, and also reducing pressure loss in the exhaust gas flow channel. Besides, when a buffer member is already disposed downstream or upstream of the pump in the apparatus, the heat exchanger can be configured using the existing buffer member. It is therefore possible to obtain the above operation advantage without increasing the cost and number of components of the apparatus.

The exhaust gas analysis apparatus preferably further includes a flowmeter designed to measure a flow rate of exhaust gas downstream of the analysis device in the exhaust gas flow channel. The flowmeter is preferably disposed downstream of the heat exchanger.

With this arrangement, the pressure fluctuations or the like is reducible by the buffer space in each of the downstream-side heat transfer part and the upstream-side heat transfer part as described above, thus leading to more accurate measurement of the flow rate of the exhaust gas.

In a specific arrangement, the upstream-side heat transfer part is disposed between the pump and the analysis device, and the downstream-side heat transfer part is disposed between the pump and the flowmeter.

In order to surely prevent the moisture condensation in the exhaust gas flow channel, the heat exchanger preferably heats the exhaust gas passing upstream of the pump in the exhaust gas flow channel to not less than a dew point of moisture contained in the exhaust gas.

In an embodiment that is intended to dilute and analyze exhaust gas discharged from the internal combustion engine, the embodiment further includes a diluter disposed in the exhaust gas flow channel and designed to permit introduction of dilution gas for diluting the exhaust gas.

The exhaust gas analysis apparatus preferably further includes a dilution gas flow channel, a second flowmeter, and a control device. The dilution gas flow channel is connected to the diluter and permits passage of the dilution gas. The second flowmeter is disposed in the dilution gas flow channel. The control device is designed to control the pump on the basis of an exhaust gas flow rate measured by the flowmeter and a dilution gas flow rate measured by the second flowmeter.

With this configuration, for example, a ratio (dividing ratio) of a flow rate of entire exhaust gas discharged from the internal combustion engine and a flow rate of exhaust gas introduced into the analysis device is highly accurately controllable in a state in which the error in exhaust gas flow rate due to the moisture condensation is reduced as described above.

According to one aspect of the present invention, an exhaust gas analysis method uses an exhaust gas analysis apparatus including an exhaust gas flow channel, a pump, a flowmeter, and a buffer member. The exhaust gas flow channel permits passage of exhaust gas of an internal combustion engine and includes an analysis device. The pump is disposed downstream of the analysis device in the exhaust gas flow channel. The flowmeter is designed to measure a flow rate of exhaust gas downstream of the analysis device in the exhaust gas flow channel. The buffer member is disposed downstream of the pump in the exhaust gas flow channel, and an interior of the buffer member is formed as a buffer space. The exhaust gas analysis method includes receiving heat generated from the pump by using the buffer member, and then transferring the heat through the buffer member to exhaust gas passing upstream of the pump in the exhaust gas flow channel.

With the above exhaust gas analysis method, the same operation advantage as the exhaust gas analysis apparatus described is obtainable while reducing, by the buffer member, the pressure fluctuations and noise caused by the pulsation of the pump, as well as the pressure loss in the exhaust gas flow channel.

Besides, when the buffer member already exists in the apparatus, the above operation advantage is obtainable without increasing the cost and number of components of the apparatus.

Effect

With the aspect of the present invention so configured, a measurement error of the flowmeter is reducible by preventing moisture condensation without causing the various problems, such as the enlarged size and high cost of the apparatus, and the increased power consumption.

DETAILED DESCRIPTION

One embodiment of an exhaust gas analysis apparatus in the present invention is described below with reference to the drawings.

The exhaust gas analysis apparatus 100 of the present embodiment is intended to analyze components contained in exhaust gas discharged from an internal combustion engine (not illustrated). Here, the exhaust gas analysis apparatus 100 is usable for measuring particulate matter (PM) in the exhaust gas. The exhaust gas analysis apparatus 100 is mountable in a vehicle that travels on a road, and it is therefore possible to measure PM contained in exhaust gas discharged from the internal combustion engine during an actual travel on a road. The exhaust gas analysis apparatus 100 is applicable not only to one which is mounted in a vehicle, but also to one which is used for test facilities including, for example, a chassis dynamometer and an engine dynamometer disposed in a test room or the like.

Figure 1:
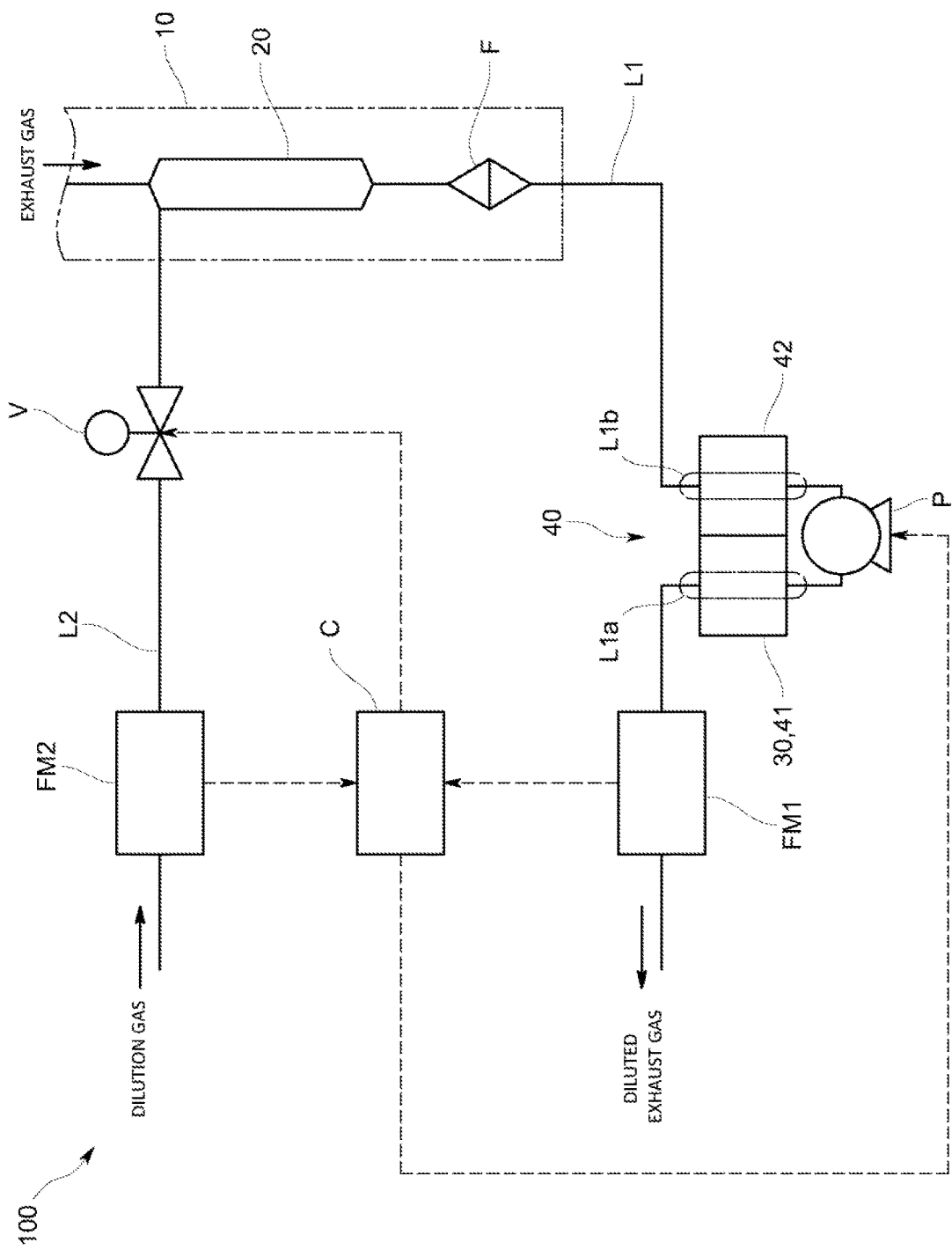
FIG. 1 is a schematic diagram illustrating a configuration of an exhaust gas analysis apparatus in the present embodiment.

Specifically, as illustrated in FIG. 1, the exhaust gas analysis apparatus 100 includes an exhaust gas flow channel L1, a dilution gas flow channel L2, an analysis device F, a heating mechanism 10, a pump P, and a flowmeter FM1 (hereinafter referred to as "first flowmeter FM1"). The exhaust gas flow channel L1 is designed to permit introduction of exhaust gas. The dilution gas flow channel L2 is designed to supply dilution gas for diluting exhaust gas to the exhaust gas flow channel L1. The analysis device F is disposed downstream of a portion of the exhaust gas flow channel L1 which connects to the dilution gas flow channel L2. The heating mechanism 10 is designed to heat at least upstream of the analysis device F in the exhaust gas flow channel L1. The pump P is disposed downstream of the analysis device F in the exhaust gas flow channel L1. The flowmeter FM1 is disposed downstream of the pump P in the exhaust gas flow channel L1.

The exhaust gas flow channel L1 includes one end disposed, for example, in an exhaust pipe of the internal combustion engine (not illustrated), and the other end through which the exhaust gas being diluted with the dilution gas is discharged to the outside.

The exhaust gas flow channel L1 of the present embodiment is designed to dividingly collect and then dilute part of the exhaust gas discharged from the internal combustion engine, and thereafter introduce an entire amount thereof to the analysis device F. Specifically, the exhaust gas flow channel L1 includes a dilution tunnel (diluter) 20, such as a micro-tunnel, and the dilution gas flow channel L2 is connected to the dilution tunnel 20.

Alternatively, the exhaust gas flow channel L1 may include a full-tunnel through which an entire amount of the exhaust gas discharged from the internal combustion engine is introduced into the dilution tunnel 20.

The dilution gas flow channel L2 is designed to introduce the dilution gas into the dilution tunnel 20. One end of the dilution gas flow channel L2 is connected to a dilution gas source (not illustrated), and the other end thereof is connected to the dilution tunnel 20.

The dilution gas flow channel L2 of the present embodiment is provided with a second flowmeter FM2, such as a venturi flowmeter and a flow rate control valve V in order to be able to control a flow rate of the dilution gas supplied to the exhaust gas flow channel L1. The dilution gas in the present embodiment is air.

The analysis device F is disposed downstream of the dilution tunnel 20 in the exhaust gas flow channel L1 and designed to measure various components contained in diluted exhaust gas. The analysis device F is a filter that captures PM contained in exhaust gas. Alternatively, the analysis device F may be an exhaust gas analysis apparatus that continuously measures exhaust gas, such as a diffusion charging method sensor (DCS), a flame ionization method detector (FID), a condensation particle counter (CPC), an electrical low pressure impactor (ELPI), or a scanning mobility particle sizer (SMPS).

The heating mechanism 10 is designed to heat upstream of at least the analysis device F in the exhaust gas flow channel L1 to a predetermined temperature (a dew point or above) at which no moisture in exhaust gas condenses. Here, the heating mechanism 10 is designed to heat the analysis device F and also upstream of the analysis device F. Specifically, the heating mechanism 10 is one which uses, for example, a heater, and switches between heating and suspension by obtaining an ON/OFF signal inputted from the outside. The heating mechanism 10 need not necessarily heat the analysis device F.

The pump P is a sampling pump for sampling the exhaust gas discharged from the internal combustion engine into the exhaust gas flow channel L1. The pump P is, for example, a suction pump (e.g. a blower) including a motor (not illustrated). Suction capability of the pump is made variable by controlling a rotation number of the motor or by means of a variable valve.

A buffer member 30 whose interior is formed as a buffer space is disposed downstream of the pump P in the present embodiment in order to reduce pressure fluctuations in the exhaust gas flow channel L1 and noise of the pump P caused by, for example, pulsation of the pump P. Specifically, the buffer member 30 is made of metal, such as aluminum, and has a hollow shape, such as a casing shape or cylinder shape. Piping constituting the exhaust gas flow channel L1 is connected to ports respectively formed on a lower surface and an upper surface of the buffer member 30. Material and shape of the buffer member 30 are not limited to the above, but may be suitably modified.

The first flowmeter FM1 is designed to measure a flow rate of exhaust gas (a flow rate of exhaust gas being diluted by the dilution gas) in the downstream of the analysis device F. The first flowmeter FM1 is disposed downstream of the buffer member 30 described above in the present embodiment. Specifically, the first flowmeter FM1 is a differential pressure flowmeter, such as a venturi flowmeter using a venturi tube. Alternatively, the first flowmeter FM1 may be one which uses a fluid resistance, such as an orifice or flow nozzle, besides the venturi tube.

The exhaust gas analysis apparatus 100 of the present embodiment includes a control device C that controls the pump P on the basis of at least a measured value obtained by the first flowmeter FM1.

The control device C is one which physically includes a CPU, memory, an A/D converter, a D/A converter, or the like, and is designed as follows. According to a program stored in a predetermined region of the memory, the CPU and peripheral devices cooperate with each other to acquire flow rate signals respectively indicating the measured values obtained by the first flowmeter FM1 and the second flowmeter FM2. The control device C controls the pump P and the flow rate control valve V on the basis of these flow rate signals.

Specifically, the control device C controls a flow rate of the dilution gas in real time so that a flow rate of entire exhaust gas discharged from the internal combustion engine (not illustrated) is proportional to a dividing ratio introduced into the dilution tunnel 20, namely, a ratio (dividing ratio) of a flow rate of entire exhaust gas discharged from the internal combustion engine and a flow rate of exhaust gas introduced into the analysis device F becomes constant. More specifically, the control device C controls the pump P and the flow rate control valve V so that a dividing ratio r represented by the following equation is made constant and a flow rate q4 introduced into the analysis device F is made constant.

$$r = q1/q2 = q1/(q4-q3)$$

where r is a dividing ratio, q1 is a flow rate (kg/s) of entire exhaust gas from an internal combustion engine, q2 is a flow rate (kg/s) of exhaust gas dividingly collected into the dilution tunnel 20, q3 is a flow rate (kg/s) of dilution gas, and q4 is a flow rate (kg/s) of exhaust gas after being diluted (passing flow rate of the analysis device F).

The flow rate of entire exhaust gas from the internal combustion engine is measured by the flow rate sensor (not illustrated) disposed in, for example, an exhaust pipe.

Because the exhaust gas sucked by the pump P is discharged after being heated by the heat of the pump P itself, a temperature difference of approximately 40-80° C. occurs in exhaust gas temperatures between the upstream and downstream of the pump P even though it depends on kind and structure of the pump P.

The exhaust gas analysis apparatus 100 of the present embodiment further includes a heat exchanger 40. The heat exchanger 40 is designed to receive at least one of heat of the pump P and heat of exhaust gas passing downstream of the pump P, and to use the heat to heat exhaust gas passing upstream of the pump P in the exhaust gas flow channel L1.

As illustrated in FIG. 1, the heat exchanger 40 is designed to transfer the heat of the exhaust gas passing downstream of the pump P in the exhaust gas flow channel L1 to the exhaust gas passing upstream of the pump P. In other words, the heat exchanger 40 carries out heat exchange between the exhaust gas passing downstream of the pump P and the exhaust gas passing upstream of the pump P in the exhaust gas flow channel L1.

Here, the exhaust gas passing upstream of the pump P is being heated to not less than a dew point of moisture contained in the exhaust gas by the heat exchanger 40. Specifically, the exhaust gas passing upstream of the pump P is being heated to approximately 22° C. The dew point is a temperature at which condensation starts during cooling of exhaust gas containing moisture. The dew point becomes higher as a moisture content becomes higher, and the dew point becomes lower as the moisture content becomes lower. The dew point becomes higher as an exhaust gas pressure becomes higher, and the dew point becomes lower as the exhaust gas pressure becomes lower. In other words, the dew point depends on a ratio of the exhaust gas discharged from the internal combustion engine and the dilution gas (namely, a dilution ratio), and a pressure in the exhaust gas flow channel L1 being decompressed by the pump P. Therefore, a heating temperature attainable by the heat exchanger 40 may be suitably changed.

Specifically, the heat exchanger 40 includes a downstream-side heat transfer part 41 located downstream of the pump P in the exhaust gas flow channel L1, and an upstream-side heat transfer part 42 which is located upstream of the pump P in the exhaust gas flow channel L1, and which is in contact with the downstream-side heat transfer part 41.

In the present embodiment, at least a part of the exhaust gas flow channel L1 is designed to extend in, for example, an identical direction (even though being upward in FIG. 1, it is possible to suitably change into downward or sideward) in each of the upstream and downstream of the pump P, and a part of the upstream of the pump P and a part of the downstream of the pump P are disposed close to each other. The heat exchanger 40 is interposed between the part of the upstream (hereinafter referred to as "an upstream-side heat exchange region L1*b*") and the part of the downstream hereinafter referred to as "a downstream-side heat exchange region L1*a*"). That is, the heat exchanger 40 is configured by disposing the upstream-side heat transfer part 42 in the upstream-side heat exchange region L1*b*, by disposing the downstream-side heat transfer part 41 in the downstream-side heat exchange region L1*a*, and by bringing the upstream-side heat transfer part 42 and the downstream-side heat transfer part 41 into contact with each other.

The exhaust gas temperature becomes lower as getting closer to an inlet side of the pump P, and the exhaust gas temperature becomes higher as getting closer to an outlet side of the pump P. Therefore, in order to improve heat exchange efficiency, the downstream-side heat transfer part 41 and the upstream-side heat transfer part 42 are preferably disposed near the pump P, and the heat exchanger 40 is preferably disposed near the pump P.

The downstream-side heat transfer part 41 is designed to be connected to the piping constituting the exhaust gas flow channel L1, and has, for example, a hollow shape, such as a casing shape or cylinder shape, which is provided with an internal space constituting a part of the exhaust gas flow channel L1.

The buffer member 30 described above is used as the downstream-side heat transfer part 41 in the present embodiment. The downstream-side transfer part 41 has both a buffer function of reducing pressure fluctuations in the exhaust gas flow channel L1 caused by, for example, the pulsation of the pump P, and a heat exchange function of receiving heat of the exhaust gas passing downstream of the pump P and then transferring the heat to the exhaust gas passing upstream of the pump P.

The upstream-side heat transfer part 42 is designed to be connected to the piping constituting the exhaust gas flow channel L1, and has, for example, a hollow shape, such as a casing shape or cylinder shape, which is provided with an internal space constituting a part of the exhaust gas flow channel L1.

The upstream-side heat transfer part 42 in the present embodiment is disposed between the pump P and the analysis device F described above in the exhaust gas flow channel L1, and is also disposed oppositely to the buffer member 30 that is the downstream-side heat transfer part 41. Specifically, the upstream-side heat transfer part 42 is made of metal, such as aluminum, and has a casing shape, in which the piping constituting the exhaust gas flow channel L1 is connected to ports respectively formed on upper and lower surfaces of the upstream-side heat transfer part 42. The upstream-side heat transfer part 42 in the present embodiment has a buffer space formed therein, and has the same configuration as the buffer member 30 that is the downstream-side heat transfer part 41. The material and shape of the upstream-side heat transfer part 42 may be suitably modified.

A surface of the upstream-side heat transfer part 42 which is opposed to the downstream-side heat transfer part 41 is formed as a heat receiving surface, and the entirety of a side surface of the downstream-side heat transfer part 41 is designed to be in contact with the heat receiving surface in the present embodiment. Alternatively, only a part of the side surface of the downstream-side heat transfer part 41 may be in contact with the heat receiving surface.

With the exhaust gas analysis apparatus 100 in the present embodiment so configured, the heat exchanger 40 uses the heat generated from the pump P to heat the exhaust gas passing upstream of the pump P. It is therefore possible to raise the temperature of the exhaust gas passing downstream of the analysis device F without disposing a heater or the like. This makes it possible to prevent moisture condensation without causing, for example, the enlarged size and high cost of the apparatus, thereby reducing a measurement error of the first flowmeter FM1, which is due to the moisture condensation.

Furthermore, the use of waste heat of the pump P leads to the high-efficient energy-saving apparatus.

Moreover, because the downstream-side heat transfer part 41 and the upstream-side heat transfer part 42 have both the buffer function and the heat exchange function, it is possible to heat the exhaust gas passing upstream of the pump P while reducing the pressure fluctuations and noise caused by the pulsation of the pump P, and also the pressure loss in the exhaust gas flow channel L1. Besides, when the buffer member 30 already exists in the apparatus, the heat exchanger 40 can be configured using the existing one. It is therefore possible to obtain the above operation advantage without increasing the cost and number of components of the apparatus.

Additionally, because the flowmeter is disposed downstream of the buffer member 30, for example, the pressure fluctuations caused by the pulsation of the pump P is reducible by the buffer member 30, thus leading to more accurate measurement of the flow rate of the exhaust gas.

The present invention is not limited to the above embodiment.

Figure 2:
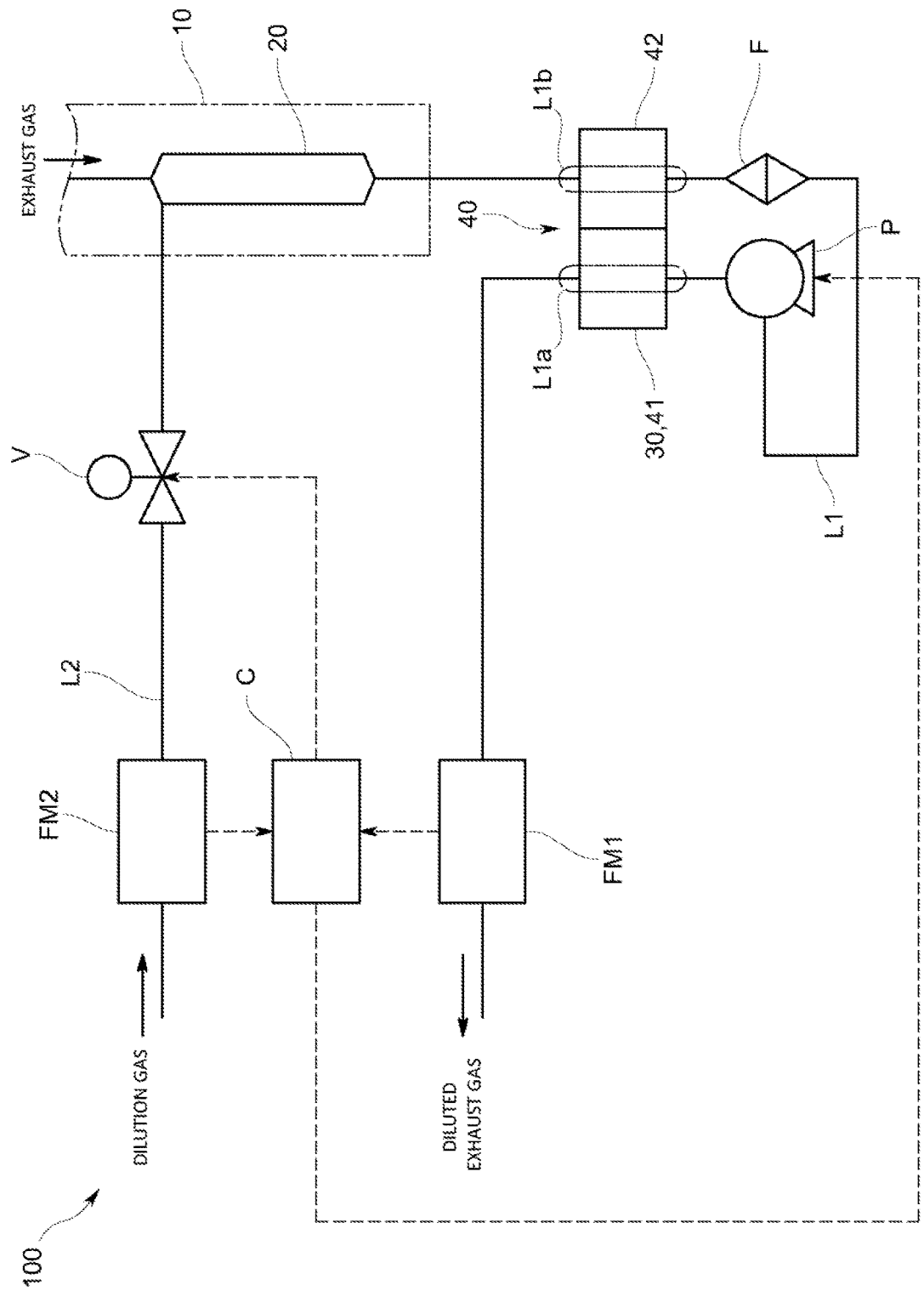
FIG. 2 is a schematic diagram illustrating a configuration of an exhaust gas analysis apparatus in a modified embodiment.

For example, even though the heat exchanger 40 is designed to heat the exhaust gas passing between the analysis device F and the pump P in the above embodiment, the heat exchanger 40 may heat the exhaust gas passing upstream of the analysis device F as illustrated in FIG. 2.

Figure 3:
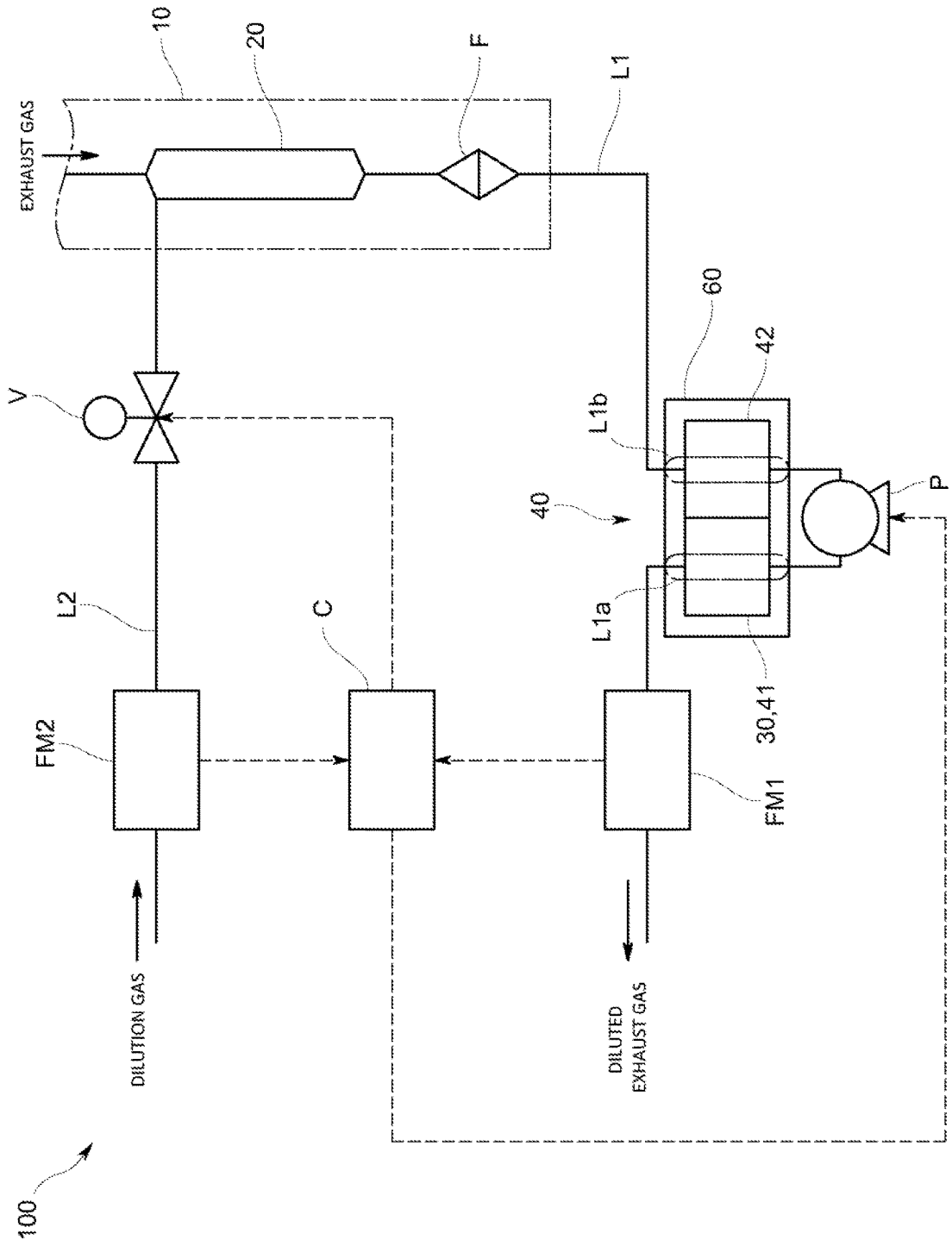
FIG. 3 is a schematic diagram illustrating a configuration of an exhaust gas analysis apparatus in another modified embodiment.

The exhaust gas analysis apparatus 100 may further include a heat insulation member 60 disposed around the heat exchanger 40 as illustrated in FIG. 3.

Use of the heat insulation member 60 makes it possible to more efficiently use the heat generated from the pump P.

Although the flowmeter is disposed downstream of the buffer member 30 in the above embodiment, the flowmeter may be disposed upstream of the pump P.

Although the buffer member 30 is used as the downstream-side heat transfer part 41 in the above embodiment, the heat exchanger 40 may be configured without using the buffer member 30. Specifically, the heat exchanger 40 may be suitably modified as long as it is designed to carry out heat exchange between the upstream and downstream of the pump P in the exhaust gas flow channel L1. For example, the heat exchanger 40 may be configured by using a metal plate member that is crossed over between the upstream and downstream of the pump P in the exhaust gas flow channel L1.

Figure 4:
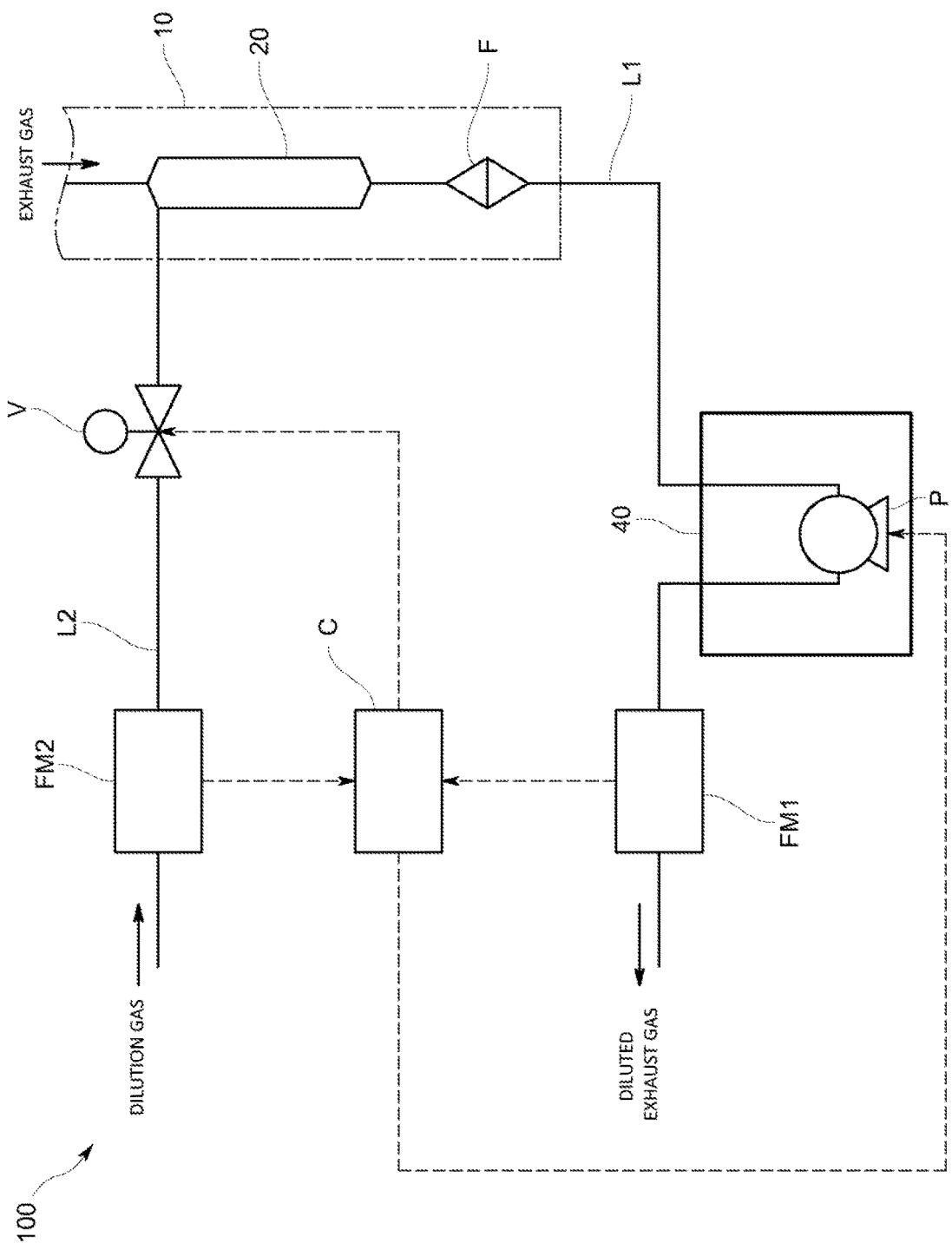
FIG. 4 is a schematic diagram illustrating a configuration of a heat exchanger in a modified embodiment.

Additionally, the heat exchanger 40 is not limited to one which is designed to receive the heat of the exhaust gas passing downward of the pump P. The heat exchanger 40 merely needs to have a configuration intended to receive the heat generated from the pump P, such as a configuration intended to receive heat released from the pump P into the atmosphere. Specifically, as the heat exchanger 40 of this type, one which is made of, for example, a heat insulating member, and surroundingly accommodates the pump P is conceivable as illustrated in FIG. 4. Thus, an internal space of the heat exchanger 40 can be heated by the heat of the pump P, thereby heating the exhaust gas passing upstream and downstream of the pump P.

Although the exhaust gas discharged from the internal combustion engine is diluted by the dilution gas in the above embodiment, the exhaust gas may be introduced into the analysis device F without being diluted.

Besides those mentioned above, it will be understood that the present invention is not limited to the above-described embodiment, and various modifications may be made without departing from the spirit and scope of the present invention.

DESCRIPTION OF THE REFERENCE NUMERALS

100 exhaust gas analysis apparatus
L1 exhaust gas flow channel
F analysis device
10 heating mechanism
P pump
FM1 first flowmeter
30 buffer member
40 heat exchanger

What is claimed is:

1. An exhaust gas analysis system comprising:
    an exhaust gas flow channel configured to permit passage of exhaust gas of an internal combustion engine and provided with an exhaust gas analysis apparatus that continuously measures the exhaust gas;
    a pump disposed downstream of the exhaust gas analysis apparatus in the exhaust gas flow channel;
    a heat exchanger configured to receive at least one of heat of the pump and heat of exhaust gas passing downstream of the pump, and to use the heat to heat exhaust gas passing upstream of the pump in the exhaust gas flow channel; and
    a first flowmeter disposed downstream of the heat exchanger and configured to measure a flow rate of exhaust gas downstream of the exhaust gas analysis apparatus in the exhaust gas flow channel.

2. The exhaust gas analysis system according to claim 1, wherein the heat exchanger comprises:
    a downstream-side heat transfer part located downstream of the pump in the exhaust gas flow channel; and
    an upstream-side heat transfer part located upstream of the pump in the exhaust gas flow channel and in contact with the downstream-side heat transfer part.

3. The exhaust gas analysis system according to claim 2, wherein at least one of the downstream-side heat transfer part and the upstream-side heat transfer part comprises a buffer space configured to reduce pressure fluctuations in the exhaust gas flow channel.

4. The exhaust gas analysis system according to claim 1, wherein the upstream-side heat transfer part is disposed between the pump and the analysis device, and the downstream-side heat transfer part is disposed between the pump and the first flowmeter.

5. The exhaust gas analysis system according to claim 1, wherein the heat exchanger is configured to heat exhaust gas passing upstream of the pump in the exhaust gas flow channel to not less than a predetermined temperature to prevent moisture condensation in the exhaust gas flow channel.

6. The exhaust gas analysis system according to claim 1, further comprising:
    a diluter disposed in the exhaust gas flow channel and configured to permit introduction of dilution gas for diluting the exhaust gas.

7. The exhaust gas analysis system according to claim 6, further comprising:
    a dilution gas flow channel connected to the diluter and configured to permit passage of the dilution gas;
    a second flowmeter disposed in the dilution gas flow channel; and
    a controller designed to control the pump on the basis of an exhaust gas flow rate measured by the first flowmeter and a dilution gas flow rate measured by the second flowmeter.

8. The exhaust gas analysis system of claim 1, wherein the exhaust gas analysis apparatus is a diffusion charging method sensor (DCS), a flame ionization method detector (FID), a condensation particle counter (CPC), an electrical low pressure impactor (ELPI), or a scanning mobility particle sizer (SMPS).

9. An exhaust gas analysis method using an exhaust gas analysis system including (i) an exhaust gas flow channel configured to permit passage of exhaust gas of an internal combustion engine and provided with an exhaust gas analysis apparatus that continuously measures the exhaust gas or a filter, (ii) a pump disposed downstream of the exhaust gas analysis apparatus or the filter in the exhaust gas flow channel, and (iii) a flowmeter disposed downstream of a heat exchanger, the exhaust gas analysis method comprising:
    heating, by the heat exchanger, exhaust gas passing upstream of the pump in the exhaust gas flow channel by using at least one of heat of the pump and heat of exhaust gas passing downstream of the pump; and
    measuring, by the flowmeter, a flow rate of exhaust downstream of the exhaust gas analysis apparatus or the filter in the exhaust has flow channel.

10. An exhaust gas system comprising: an exhaust gas flow channel configured to permit passage of exhaust gas of an internal combustion engine and provided with a filter configured to capture particulate matter contained in the exhaust gas;
    a pump disposed downstream of the filter in the exhaust gas flow channel;
    a heat exchanger configured to receive at least one of heat of the pump and heat of exhaust gas passing downstream of the pump, and to use the heat to heat exhaust gas passing upstream of the pump in the exhaust gas flow channel; and a first flowmeter disposed downstream of the heat exchanger and configured to measure a flow rate of exhaust gas downstream of the filter in the exhaust gas flow channel.

11. The exhaust gas analysis system according to claim 10, wherein the heat exchanger comprises:
   a downstream-side heat transfer part located downstream of the pump in the exhaust gas flow channel; and
   an upstream-side heat transfer part located upstream of the pump in the exhaust gas flow channel and in contact with the downstream-side heat transfer part.

12. The exhaust gas system according to claim 11, wherein at least one of the downstream-side heat transfer part and the upstream-side heat transfer part comprises a buffer space configured to reduce pressure fluctuations in the exhaust gas flow channel.

13. The exhaust gas system according to claim 10, wherein the upstream-side heat transfer part is disposed between the pump and the filter, and the downstream-side heat transfer part is disposed between the pump and the first flowmeter.

14. The exhaust gas system according to claim 10, wherein the heat exchanger is configured to heat exhaust gas passing upstream of the pump in the exhaust gas flow channel to not less than a predetermined temperature to prevent moisture condensation in the exhaust gas flow channel.

15. The exhaust gas system according to claim 10, further comprising:
   a diluter disposed in the exhaust gas flow channel and configured to permit introduction of dilution gas for diluting the exhaust gas.

16. The exhaust gas system according to claim 15, further comprising:
   a dilution gas flow channel connected to the diluter and configured to permit passage of the dilution gas;
   a second flowmeter disposed in the dilution gas flow channel; and
   a controller designed to control the pump on the basis of an exhaust gas flow rate measured by the first flow meter and a dilution gas flow rate measured by the second flowmeter.

* * * * *